US012672895B2

(12) United States Patent
Shen

(10) Patent No.: US 12,672,895 B2
(45) Date of Patent: Jul. 7, 2026

(54) CORONARY ARTERY ROTATIONAL ATHERECTOMY INTERVENTION SYSTEM

(71) Applicant: Guangzhou Bossh Medical Technology Co., Ltd., Guangzhou (CN)

(72) Inventor: Bin Shen, Shanghai (CN)

(73) Assignee: Guangzhou Bossh Medical Technology Co., Ltd., Guangzhou (CN)

( * ) Notice: Subject to any disclaimer, the term of this patent is extended or adjusted under 35 U.S.C. 154(b) by 51 days.

(21) Appl. No.: 18/950,236

(22) Filed: Nov. 18, 2024

(65) Prior Publication Data

US 2025/0072930 A1      Mar. 6, 2025

Related U.S. Application Data

(63) Continuation of application No. PCT/CN2022/093165, filed on May 16, 2022.

(51) Int. Cl.
| | |
|---|---|
| *A61B 17/3207* | (2006.01) |
| *A61B 17/00* | (2006.01) |
| *A61B 90/00* | (2016.01) |

(52) U.S. Cl.
CPC ...... *A61B 17/320758* (2013.01); *A61B 90/03* (2016.02); *A61B 2017/00022* (2013.01);
(Continued)

(58) Field of Classification Search
CPC ................ A61B 17/22; A61B 17/3207; A61B 17/320758; A61B 2017/00017;
(Continued)

(56) References Cited

U.S. PATENT DOCUMENTS

| | | | |
|---|---|---|---|
| 2014/0163384 A1* | 6/2014 | Torrance | ................ A61M 1/71 |
| | | | 600/585 |
| 2021/0077143 A1* | 3/2021 | Neuharth | ....... A61B 17/320758 |
| 2021/0236158 A1* | 8/2021 | Rawson | ............... A61M 25/09 |

FOREIGN PATENT DOCUMENTS

| | | |
|---|---|---|
| CN | 101522115 A | 9/2009 |
| CN | 102325502 A | 1/2012 |
| | (Continued) | |

OTHER PUBLICATIONS

International Search Report of PCT Patent Application No. PCT/CN2022/093165 issued on Dec. 29, 2022.

*Primary Examiner* — Mohamed G Gabr

(57) ABSTRACT

In a coronary artery rotational atherectomy intervention system provided in this application, a limit switch in a guide wire clamping system is connected to a limit switch state detection and transmission module. After the guide wire is clamped, the limit switch is triggered to be in a closed state and detected by the module. In a physiological saline infusion system, an infusion pump control element controls the infusion pump to start, and the pump is connected to an infusion pump state detection and transmission module to detect its started state. Before issuing an instruction for starting a drive motor, a controller module in the drive and control system confirms that the infusion pump is started and the limit switch is closed, to drive the rotational atherectomy head to rotate, thereby remarkably improving the apparatus's operational safety.

19 Claims, 9 Drawing Sheets

(52) U.S. Cl.
CPC .............. *A61B 2017/00119* (2013.01); *A61B 2017/00398* (2013.01); *A61B 2017/00477* (2013.01); *A61B 2017/00862* (2013.01); *A61B 2017/320766* (2013.01); *A61B 2090/034* (2016.02); *A61B 2217/007* (2013.01)

(58) Field of Classification Search
CPC ........... A61B 2017/00022; A61B 2017/00119; A61B 2017/00398; A61B 2017/00477; A61B 2017/00862; A61B 2017/320004; A61B 2017/320766; A61B 2090/034; A61B 2217/007; A61B 90/03
See application file for complete search history.

(56) References Cited

FOREIGN PATENT DOCUMENTS

| CN | 210903128 U | 7/2020 |
| CN | 114159131 A | 3/2022 |
| WO | 2004080507 A2 | 9/2004 |

* cited by examiner

32

322

CORONARY ARTERY ROTATIONAL ATHERECTOMY INTERVENTION SYSTEM

CROSS REFERENCE TO RELATED APPLICATIONS

The present application is a Continuation Applications of PCT Application No. PCT/CN2022/093165 filed on May 16, 2022, the contents of which are incorporated herein by reference in their entirety.

TECHNICAL FIELD

This application relates to the field of medical apparatus technologies, and specifically, to a coronary artery rotational atherectomy intervention system.

BACKGROUND

A plaque in a coronary artery of an organism (such as a human body) is an occlusion generated by deposition of calcium ions in a blood vessel of the artery on an inner wall of the blood vessel, and the occlusion slows down or even blocks the flow of blood, thereby triggering a series of ischemic heart diseases. A coronary artery rotational atherectomy intervention system is an apparatus in which an interventional therapy is used, a rotational atherectomy head rotates at a high speed to rotationally grind the plaque into tiny particles, and then the tiny particles are absorbed by a human body, thereby treating a calcified lesion of the coronary artery.

During the interventional rotational atherectomy treatment, a guide wire is first inserted into the lesioned coronary artery, then a drive shaft with the rotational atherectomy head penetrates into a lesioned position along the guide wire, a motor is started, and the rotational atherectomy head rotates at a high speed to grind the calcified plaque. Debris of the plaque rotationally ground is small in size, does not block capillaries, and is finally cleared by macrophages through phagocytosis. The rotational atherectomy head feeds back and forth, so that the tissue of the calcified plaque can be rotationally ground for a distance, to finally complete the interventional therapy of the calcified lesion of the coronary artery. During the interventional therapy, the temperature increase caused by the high-speed rotation of the rotational atherectomy head is reduced through the infusion of the physiological saline, to avoid affecting a normal in-vivo temperature environment of the patient.

SUMMARY

Based on the foregoing current situation, a main objective of this application is to provide a coronary artery rotational atherectomy intervention system, to significantly improve operation safety of the coronary artery rotational atherectomy intervention system.

To achieve the foregoing objective, the technical solutions adopted in this application are as follows:

This application provides a coronary artery rotational atherectomy intervention system, including a rotational atherectomy mechanism, a physiological saline infusion system, a drive and control system, and a guide wire clamping system, where the rotational atherectomy mechanism includes a guide wire, a drive shaft assembly, and a rotational atherectomy head, the guide wire clamping system includes a limit switch and a limit switch state detection and transmission module, the limit switch is connected to the limit switch state detection and transmission module, and after the guide wire is clamped, the limit switch is triggered to be in a closed state and is detected by the limit switch state detection and transmission module;

the physiological saline infusion system includes an infusion pump, an infusion pump control element, and an infusion pump state detection and transmission module, the infusion pump control element is connected to the infusion pump, the infusion pump control element is configured to control the infusion pump to be in a started state, and the infusion pump is connected to the infusion pump state detection and transmission module, to enable the started state of the infusion pump to be detected by the infusion pump state detection and transmission module;

the drive and control system includes a drive motor and a controller module, and the limit switch state detection and transmission module and the infusion pump state detection and transmission module are separately connected to the controller module to transmit state data to the controller module; and the controller module confirms, before issuing an instruction for starting the drive motor, that the infusion pump of the physiological saline infusion system is in the started state and the limit switch is in the closed state, to cause the drive motor to rotate and then drive the rotational atherectomy head to rotate together through the drive shaft assembly.

Preferably, the drive shaft assembly includes a drive shaft, the drive shaft includes a rigid shaft and a flexible shaft, the flexible shaft is fixedly connected to a front side of the rigid shaft, the rotational atherectomy head is formed at an end of the flexible shaft away from the rigid shaft, and the rotational atherectomy head includes an eccentric structure in a circumferential direction around the flexible shaft; the eccentric structure includes a cylindrical segment, and in different radial directions of a cross segment of the cylindrical segment, a connecting line between a first point on an outer wall surface of the cylindrical segment closest to a central axis of the flexible shaft and a second point on the outer wall surface of the cylindrical segment farthest from the central axis of the flexible shaft intersects with the central axis of the flexible shaft; and a straight-line distance between the first point and the second point ranges from 0.8 mm to 1.2 mm, and a difference between a distance from the second point to the central axis and a distance from the first point to the central axis ranges from 0.05 mm to 0.2 mm.

Preferably, the straight-line distance between the first point and the second point is 0.9 mm, and the difference between the distance from the second point to the central axis and the distance from the first point to the central axis is 0.1 mm.

Preferably, the rotational atherectomy head further includes a tapered portion located at a front end of the eccentric structure, the tapered portion is coaxial with the flexible shaft, a major diameter end of the tapered portion is connected to the eccentric structure, and the eccentric structure further includes a first eccentric cone segment and a second eccentric cone segment located at a front end and a rear end of the cylindrical segment respectively, where a minor diameter end of the first eccentric cone segment is connected to the major diameter end of the tapered portion, a major diameter end of the first eccentric cone segment is connected to the front end of the cylindrical segment, a major diameter end of the second eccentric cone segment is connected to the rear end of the cylindrical segment, and a minor diameter end of the second eccentric cone segment is connected to an outer circumferential surface of the flexible shaft; the tapered portion is made of stainless steel, and has an outer surface being a smooth surface; and the eccentric structure includes an electroformed nickel substrate and abrasive particles inlaid in the substrate by electroplating.

Preferably, an axial dimension of the tapered portion accounts for 30% to 40% of an axial dimension of the rotational atherectomy head, an axial dimension of the cylindrical segment accounts for 40% to 50% of the axial dimension of the rotational atherectomy head, and a ratio of a diameter of the cylindrical segment to an axial dimension of the eccentric structure ranges from 0.6 to 0.7.

Preferably, after the infusion pump control element controls the infusion pump to start, the infusion pump state detection and transmission module sends a first indication signal to the controller module, to enable the controller module to confirm that the infusion pump is in the started state.

Preferably, the drive and control system further includes an optical coupler, the optical coupler is located between the infusion pump state detection and transmission module and the controller module, and the optical coupler receives the first indication signal, processes the first indication signal, and transmits the first indication signal to the controller module.

Preferably, after the limit switch is closed, the limit switch state detection and transmission module sends a second indication signal to the controller module, to enable the controller module to confirm that the limit switch is in the closed state.

Preferably, the drive and control system further includes a motor drive module and a speed detection module, the controller module is connected to both the motor drive module and the speed detection module, the drive motor is connected to both the motor drive module and the speed detection module, the motor drive module drives the drive motor under the control of the controller module, and the speed detection module feeds back real-time speed information of the drive motor to the controller module; and when a rotation speed of the drive motor measured in real time is greater than or less than a preset speed, the controller module in the drive and control system controls the motor drive module to adjust the rotation speed of the drive motor to the preset speed.

Preferably, the drive and control system further includes a display screen, a multi-range knob switch, a range information processing module, and a motor drive module, where the multi-range knob switch is connected to the range information processing module, the range information processing module is connected to the controller module, the controller module is connected to the motor drive module, the motor drive module is connected to the drive motor to control a rotation speed of the drive motor to be in a selected range, and the display screen is arranged at an angle of 30 degrees to a horizontal plane, and is configured to display the rotation speed of the drive motor and a rotational atherectomy time.

Preferably, the drive and control system further includes a sampling resistor, a sampling resistor voltage collection module, an amplifier, an amplified voltage information transmission module, and a motor drive module, where the drive motor is connected to the sampling resistor, the sampling resistor is connected to the sampling resistor voltage collection module, the sampling resistor voltage collection module is connected to the amplifier, the amplifier is connected to the amplified voltage information transmission module, the amplified voltage information transmission module is connected to the controller module, the controller module is connected to the motor drive module, the motor drive module is connected to the drive motor, and when overload occurs, the controller module controls the motor drive module to stop driving the drive motor, to cause the drive motor to stop running.

Preferably, the drive and control system further includes a motor drive module; the physiological saline infusion system further includes a plurality of flow rate adjustment circuits and a physiological saline infusion control motor, the plurality of flow rate adjustment circuits include a plurality of resistors and a plurality of flow rate selector switches, resistance values of the plurality of resistors are different from each other, quantities of the flow rate adjustment circuits, the flow rate selector switches, and the resistors are the same, one flow rate selector switch and one resistor are serially connected in a same flow rate adjustment circuit, and each flow rate adjustment circuit is connected to the controller module; and the controller module is connected to the physiological saline infusion control motor, to control a rotation speed of the physiological saline infusion control motor, to further control an infusion speed of physiological saline.

Preferably, the physiological saline infusion control motor drives the infusion pump, a rotation speed of the infusion pump is increased or decreased as the rotation speed of the physiological saline infusion control motor is increased or decreased, and the infusion speed of the physiological saline is increased or decreased as the rotation speed of the infusion pump is changed, to control the infusion speed of the physiological saline.

Preferably, the drive shaft assembly includes a drive shaft and a drive shaft sleeve; the drive and control system further includes a driving gear and a transmission gear, a part of the drive shaft is fixedly mounted in the transmission gear, and at least one part of remaining parts of the drive shaft that are not fixedly mounted in the transmission gear, and at least one part of the guide wire are located in the drive shaft sleeve; the drive shaft sleeve includes a front sleeve and a rear sleeve, the front sleeve includes a front moving rail tube and a front static rail tube that are nested, and the front sleeve is located in front of the transmission gear; the rear sleeve includes a rear moving rail tube and a rear static rail tube that are nested, and the rear sleeve is located behind the transmission gear; and a first wear-resistant tube exists between the drive shaft and the front moving rail tube, and/or a second wear-resistant tube exists between the drive shaft and the rear moving rail tube, and/or a wear-resistant coating is provided on at least one part of an outer surface of the drive shaft.

Preferably, a flexible seal ring is arranged outside the front moving rail tube, where an inner diameter of the seal ring is less than an outer diameter of the front moving rail tube in a natural state; and a flexible seal ring is arranged outside the rear moving rail tube, where an inner diameter of the seal ring is less than an outer diameter of the rear moving rail tube in a natural state.

Preferably, the limit switch is fixed relative to a rear wall of a housing of the coronary artery rotational atherectomy intervention system, and extends out of the rear wall; and the guide wire clamping system includes a multi-claw chuck, a chuck cover, and a chuck cover fixing base, where the multi-claw chuck includes a chucking portion formed by a plurality of independent claws and a body portion that is configured to fixedly connect the plurality of independent claws, the body portion is arranged inside the chuck cover, and the chucking portion extends into the chuck cover fixing base;

the chuck cover fixing base is fixed relative to the rear wall, a part of the chuck cover fixing base located behind the rear wall has an external thread, a rear opening of the chuck cover fixing base is configured for the chucking portion to extend, and the rear opening includes a tapered multi-claw chuck clamping portion;

an internal thread matching the external thread exists inside the chuck cover, and the chuck cover is fixed on the chuck cover fixing base through the matching between the internal thread and the external thread;

the multi-claw chuck is elastic, the chucking portion of the multi-claw chuck is opened after the guide wire is inserted into the multi-claw chuck, interference fit is formed between the multi-claw chuck clamping portion and the opened chucking portion after the chuck cover is tightened relative to the chuck cover fixing base, and the interference fit clamps the chucking portion, to cause the guide wire to be clamped by the multi-claw chuck; and after the chuck cover is tightened relative to the chuck cover fixing base, a front end surface of the chuck cover presses the limit switch, to trigger the limit switch to be in the closed state.

Preferably, the chuck cover includes a cylindrical first stop structure, a second stop structure is further arranged inside the chuck cover, and after the chuck cover is tightened relative to the chuck cover fixing base, the first stop structure and the second stop structure are configured to stop the multi-claw chuck from moving backward.

Preferably, the guide wire clamping system further includes a flexible sealing structure, the flexible sealing structure includes a first via for the guide wire to pass through, a diameter of the first via is not greater than a diameter of the guide wire in a natural state, the flexible sealing structure is located inside the chuck cover and behind the second stop structure, and a front end surface of the flexible sealing structure abuts against a rear end surface of the second stop structure.

Preferably, the drive and control system further includes a timing module and an alarm apparatus that are connected to the controller module, the timing module is configured to time rotation of the drive motor, and when a single rotation time of the drive motor reaches first preset duration or a plurality of accumulated rotation times reaches second preset duration, the controller module controls the alarm apparatus to issue an alarm.

In the coronary artery rotational atherectomy intervention system in this application, before the drive motor is started to enable a rotational atherectomy apparatus to start a rotational atherectomy operation on a plaque inside a blood vessel of an organism, whether the infusion pump of the physiological saline infusion system is in the started state and whether the limit switch is in the closed state are first determined. In this way, great damage to the human body caused by starting the rotational atherectomy operation when no physiological saline is supplied or the guide wire is not clamped is avoided, and health and safety of the human body are effectively ensured. There is no need to specially apply manpower to check whether the physiological saline can be normally supplied or whether the guide wire is clamped, which obviously optimizes the operation convenience and effectively improves the operation experience.

Other beneficial effects of this application are described in the specific implementations through the introduction of specific technical features and technical solutions. A person skilled in the art can understand the beneficial technical effects brought by the technical features and technical solutions through the introduction of the technical features and technical solutions.

BRIEF DESCRIPTION OF THE DRAWINGS

The preferable implementations of this application are described below with reference to the accompanying drawings. In the accompanying drawings.

DESCRIPTIONS OF REFERENCE NUMERALS

Figure 1:
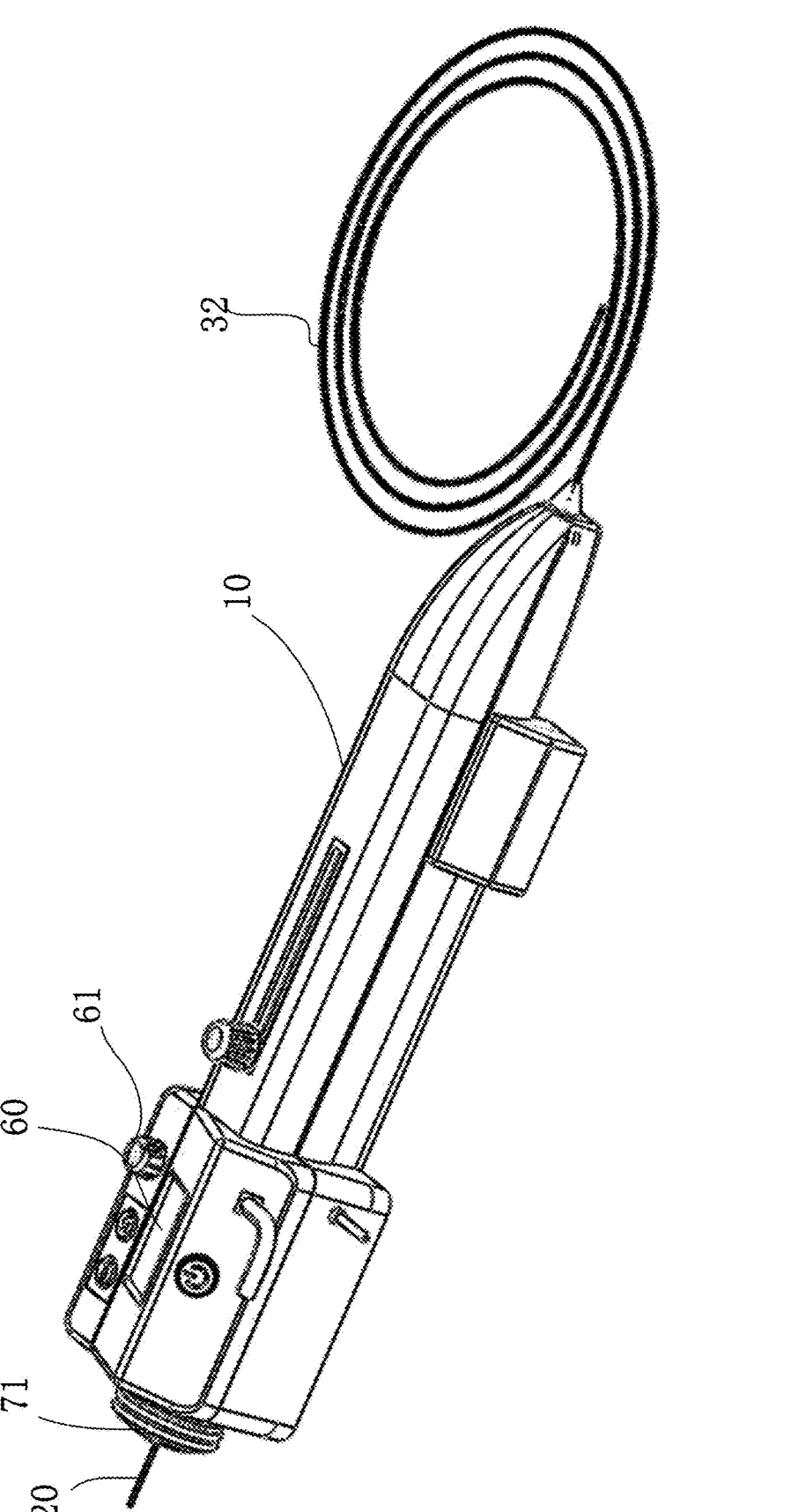
FIG. 1 is a three-dimensional schematic structural diagram of a preferred implementation of a coronary artery rotational atherectomy intervention system (an infusion pump and a physiological saline infusion control motor are not shown) according to this application.

| Reference numeral | Name | Reference numeral | Name | Reference numeral | Name |
|---|---|---|---|---|---|
| 10 | Housing | 322 | rotational atherectomy head | 741 | First via |
| 20 | Guide wire | 45 | Flexible seal ring | 75 | Second stop structure |

-continued

| Reference numeral | Name | Reference numeral | Name | Reference numeral | Name |
|---|---|---|---|---|---|
| 30 | drive shaft | 50 | Drive motor | 11 | Second via |
| 31 | Rigid shaft | 60 | Display screen | 80 | Intervention catheter |
| 32 | Flexible shaft | 61 | Multi-range knob switch | 90 | Adapter |
| 321 | Eccentric structure | 70 | Limit switch | 91 | Adapter front |
| 321a | Cylindrical segment | 71 | Chuck cover | 92 | Adapter diameter reduction structure |
| 321b | First eccentric cone segment | 72 | Chuck cover fixing base | 93 | Adapter rear |
| 321c | Second eccentric cone segment | 73 | Multi-claw chuck | 100 | Output connector |
| 322a | Tapered portion | 731 | Chucking portion | 101 | Output connector body portion |
| 41 | Front moving rail tube | 732 | Body portion | 102 | Snap head |
| 42 | Front static rail tube | 721 | Rear opening | 103 | Output connector front |
| 43 | Rear moving rail tube | 721a | Multi-claw chuck clamping portion | 104 | Output connector diameter reduction portion |
| 44 | Rear static rail tube | 711 | First stop structure | 105 | Output connector rear |
| | | 74 | Flexible sealing structure | | |

DETAILED DESCRIPTION

The following describes this application based on the embodiments, but this application is not merely limited to the embodiments. Some specified details are described in the following detailed descriptions of this application. To prevent the essence of this application from being confused, well-known methods, procedures, processes, and elements are not described in detail.

In addition, a person of ordinary skill in the art should understand that the accompanying drawings provided herein are for illustrative purposes, and the accompanying drawings are not necessarily drawn to scale.

Unless clearly required in the context otherwise, throughout the specification and the claims, "include", "comprise", and similar terms should be interpreted in an inclusive sense rather than an exclusive or exhaustive sense, that is, in a meaning of "including, but not limited to".

In the description of this application, it should be understood that, the terms "first", "second" and the like are used for the purpose of description only and are not to be construed as indicating or implying relative importance. Moreover, in the descriptions of this application, unless otherwise noted, "a plurality of" means two or more.

Description: In this application, when a coronary artery rotational atherectomy intervention system is used, an end closer to the interior of a human body is referred to as "front", and the other end is referred to as "rear". In addition, a "housing" of the coronary artery rotational atherectomy intervention system in this application is used as a common support component or protective component for a plurality of components, thereby providing protection for components mounted inside the housing. The term "housing" does not require that any component of the coronary artery rotational atherectomy intervention system be located inside the housing.

The coronary artery rotational atherectomy intervention system provided in this application, referring to FIG. 1 to FIG. 10, includes a rotational atherectomy mechanism, a physiological saline infusion system, a drive and control system, and a guide wire clamping system, where the rotational atherectomy mechanism includes a guide wire 20, a drive shaft assembly, and a rotational atherectomy head 322, the guide wire clamping system includes a limit switch 70 and a limit switch state detection and transmission module, the limit switch 70 is connected to the limit switch state detection and transmission module, and after the guide wire 20 is clamped, the limit switch 70 is triggered to be in a closed state and is detected by the limit switch state detection and transmission module;

the physiological saline infusion system includes an infusion pump (which is usually located outside the housing 10, and is not shown in the figure), an infusion pump control element, and an infusion pump state detection and transmission module, the infusion pump control element is connected to the infusion pump, the infusion pump control element is configured to control the infusion pump to be in a started state, and the infusion pump is connected to the infusion pump state detection and transmission module, to enable the started state of the infusion pump to be detected by the infusion pump state detection and transmission module;

the drive and control system includes a drive motor 50 and a controller module, and the limit switch state detection and transmission module and the infusion pump state detection and transmission module are separately connected to the controller module to transmit state data to the controller module; and the controller module confirms, before issuing an instruction for starting the drive motor 50, that the infusion pump of the physiological saline infusion system is in the started state and the limit switch is in the closed state, to cause the drive motor 50 to rotate and then drive the rotational atherectomy head 322 to rotate together through the drive shaft assembly.

Specifically, the guide wire 20 penetrates through the housing 10 of the coronary artery rotational atherectomy intervention system, and extends from a foremost end to a rearmost end of the coronary artery rotational atherectomy intervention system, a foremost end of the guide wire 20 extends out of a foremost end of the housing 10 of the coronary artery rotational atherectomy intervention system, and an end of the guide wire 20 extends out of a rearmost end of the housing 10 of the coronary artery rotational atherectomy intervention system. The guide wire 20 is a rail for sliding of the drive shaft assembly, and guides sliding of the drive shaft assembly. In a working process of the coronary artery rotational atherectomy intervention system, the guide wire 20 is used to guide the rotational atherectomy head 322 to accurately reach an operating position. In addition, by supplying physiological saline, a temperature of the rotational atherectomy apparatus is reduced during working, and blood of the organism is prevented from flowing back into the interior of the coronary artery rotational atherectomy intervention system. In the coronary artery rotational atherectomy intervention system in this application, before the drive motor 50 is started to enable a rotational atherectomy apparatus to start a rotational atherectomy operation on a plaque inside a blood vessel of an organism, whether the infusion pump of the physiological saline infusion system is in the started state and whether the limit switch 70 is in the closed state are first determined. In this way, great damage to the human body caused by starting the rotational atherectomy operation when no physiological saline is supplied or the guide wire is not clamped is avoided, and health and safety of the human body are effectively ensured. There is no need to specially apply manpower to check whether the physiological saline can be normally supplied or whether the guide wire is clamped, which obviously optimizes the operation convenience and effectively improves the operation experience.

Preferably, referring to FIG. 1 and FIG. 3 to FIG. 5, the drive shaft assembly includes a drive shaft 30, the drive shaft includes a rigid shaft 31 and a flexible shaft 32, the flexible shaft 32 is fixedly connected to a front side of the rigid shaft 31, the rotational atherectomy head 322 is formed at an end of the flexible shaft 32 away from the rigid shaft 31, and the rotational atherectomy head 322 includes an eccentric structure 321 in a circumferential direction around the flexible shaft 32; the eccentric structure 321 includes a cylindrical segment 321a, and in different radial directions of a cross segment of the cylindrical segment 321a, a straight line that can be formed by connecting a first point on an outer wall surface of the cylindrical segment closest to a central axis of the flexible shaft and a second point on the outer wall surface of the cylindrical segment farthest from the central axis of the flexible shaft intersects with the central axis of the flexible shaft; and a straight-line distance H between the first point and the second point ranges from 0.8 mm to 1.2 mm, and a difference between a distance L2 from the second point to the central axis and a distance L1 from the first point to the central axis ranges from 0.05 mm to 0.2 mm.

Preferably, the straight-line distance between the first point and the second point is 0.9 mm, and the difference between the distance from the second point to the central axis and the distance from the first point to the central axis is 0.1 mm.

Figure 7:
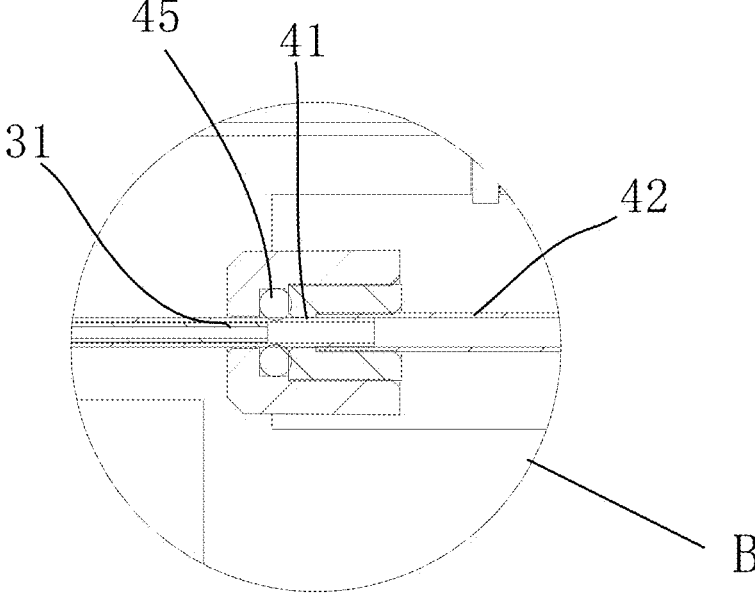
FIG. 7 is a partially enlarged schematic structural diagram of a position B in FIG. 1.
Figure 8:
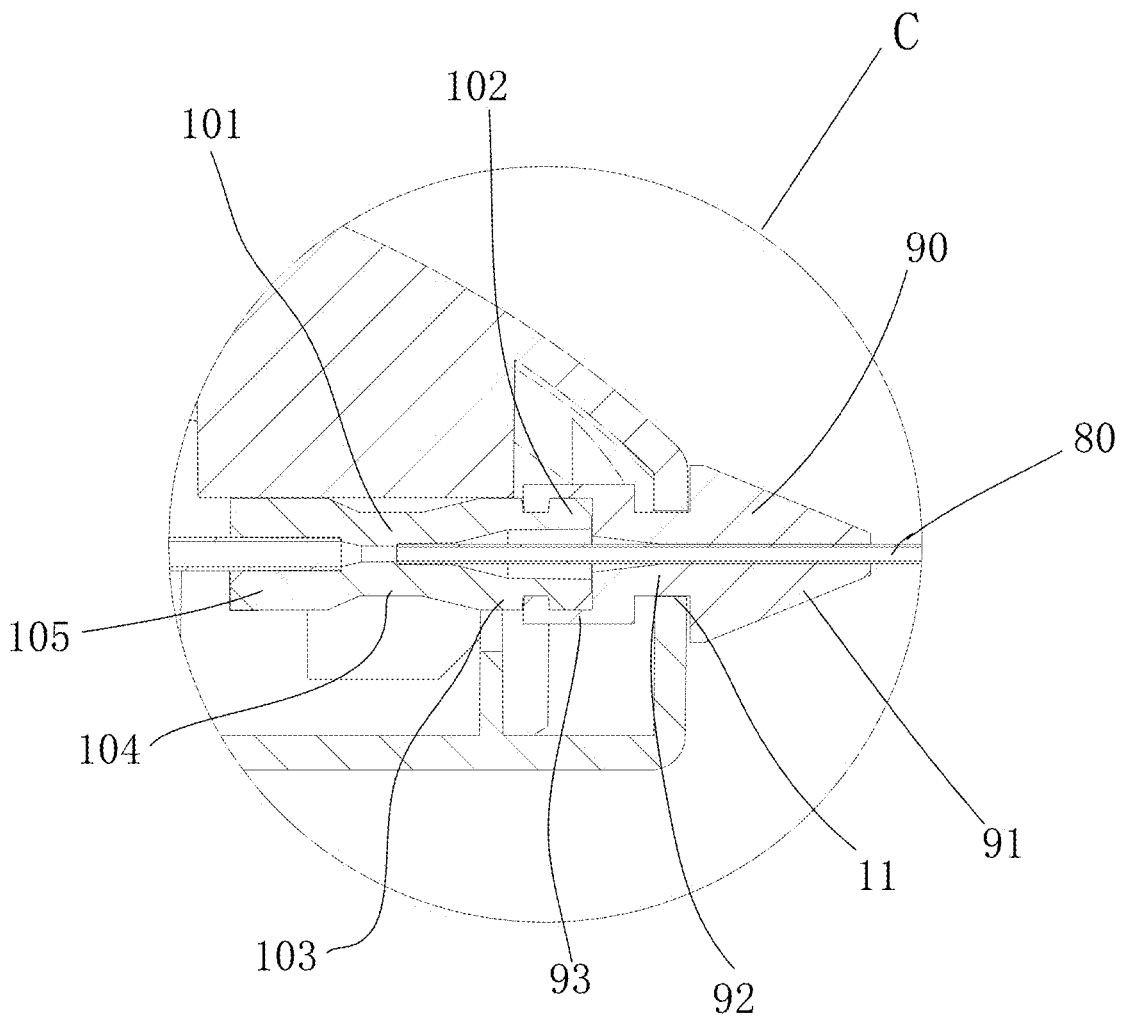
FIG. 8 is a partially enlarged schematic structural diagram of a position C in FIG. 1.

Specifically, the flexible shaft 32 is connected to the rigid shaft 31 (referring to FIG. 7, a front end of the rigid shaft 31 is shown in FIG. 7, and the flexible shaft 32 may be connected to the rigid shaft at the front end), for example, is inserted to create interference fit or welded. The flexible shaft may include an inner spring wire and an outer spring wire that are fit, and the inner spring wire and the outer spring wire are in interference fit. There are a plurality of inner spring wires helically wound around and fit each other, there are a plurality of outer spring wires helically wound around outer surfaces of the inner spring wires and fit each other, and a spiral winding direction of the outer spring wires is opposite to that of the inner spring wires. In addition, at two ends of the flexible shaft, the outer spring wires are connected by laser welding, and the inner spring wires are connected by laser welding. In addition, the inner spring wires and the outer spring wires are also connected by laser welding. That is to say, at the two ends of the flexible shaft, the spring wires are welded together, and may be specifically ground after being welded, so that an end surface thereof is flat and a surface thereof is smooth.

The rotational atherectomy head 322 is formed at an end of the flexible shaft 32 away from the rigid shaft 31. The rotational atherectomy head 322 includes an eccentric structure 321 surrounding the flexible shaft 32 in a circumferential direction, and the eccentric structure includes a cylindrical segment 321a. Longest distances from an outer wall surface of the cylindrical segment 321a to the central axis of the flexible shaft 32 are different in different radial directions of a cross segment of the cylindrical segment 321a, while longest distances from the outer wall surface of the cylindrical segment 321a to the central axis of the flexible shaft 32 are the same in the axial direction of the flexible shaft 32.

In different radial directions of a cross segment of the cylindrical segment 321a, a straight line that intersects with the central axis of the flexible shaft 32 can be formed by connecting a first point on an outer wall surface of the cylindrical segment 321a closest to a central axis of the flexible shaft 32 and a second point on the outer wall surface of the cylindrical segment farthest from the central axis of the flexible shaft 32. That is to say, a first radial direction formed by connecting the first point and a center point of a same cross segment of the flexible shaft is separated from a second radial direction formed by connecting the second point and the center point by 180°.

A diameter of the flexible shaft 32 may range from 0.5 to 0.8 mm, and is preferably 0.65 mm; a straight-line distance between the first point and the second point may range from 0.8 to 1.2 mm, and is preferably 0.9 mm; and a difference between the distance from the second point to the central axis and the distance from the first point to the central axis ranges from 0.08 to 0.16 mm, and is preferably 0.1 mm. The distance between the second point and the central axis of the flexible shaft 32 is slightly greater than the radius of the flexible shaft 32. The reason is as follows: To ensure a relatively small size, the rotational atherectomy head of this application is machined by electroplating, and it is difficult for a mold to completely protect and cover a part of the outer surface of the flexible shaft. Therefore, the rotational atherectomy head is usually formed in the entire circumferential direction of the flexible shaft. The foregoing "the distance between the second point and the central axis of the flexible shaft is slightly greater than the radius of the flexible shaft" is an inevitable result caused by this machining manner.

Preferably, the rotational atherectomy head 322 further includes a tapered portion 322a located at a front end of the eccentric structure 321, the tapered portion 322a is coaxial with the flexible shaft 32, a major diameter end of the tapered portion 322a is connected to the eccentric structure 321, and the eccentric structure 321 further includes a first eccentric cone segment 321b and a second eccentric cone segment 321c located at a front end and a rear end of the cylindrical segment 321a respectively, where a minor diameter end of the first eccentric cone segment 321b is connected to the major diameter end of the tapered portion 322a, a major diameter end of the first eccentric cone segment 321b is connected to the front end of the cylindrical segment 321a, a major diameter end of the second eccentric cone segment 321c is connected to the rear end of the cylindrical segment 321a, and a minor diameter end of the second eccentric cone segment 321c is connected to an outer circumferential surface of the flexible shaft 32; the tapered portion 322a is made of stainless steel, and has an outer surface being a smooth surface; and the eccentric structure 321 includes an electroformed nickel substrate and abrasive particles inlaid in the substrate by electroplating. In another implementation, the tapered portion 322a and the eccentric structure 321 may alternatively not be connected to each other, and may have a specific interval between each other. An interval length may be, for example, 5 mm or 8 mm.

In the axial direction of the flexible shaft, an extension length of the cylindrical segment 321a may range from 0.8 to 1.5 mm, and is preferably 1 mm. Both the first eccentric cone segment 321b and the second eccentric cone segment 321c are integrally formed with the cylindrical segment 321a, and then the first eccentric cone segment 321b and the second eccentric cone segment 321c are formed by grinding. A length of each eccentric cone segment may range from 0.1 to 0.3 mm, and is preferably 0.2 mm. The eccentric cone segment and the tapered portion are arranged, so that there is no vertical step between the rotational atherectomy head 322 and the flexible shaft 32, making it convenient for the rotational atherectomy head to enter a plaque to be rotationally ground inside a blood vessel and smoothly push a part of the plaque onto an outer wall surface of the rotational atherectomy head for rotational atherectomy.

An extension length of the tapered portion 322a ranges from 0.6 to 1.0 mm, and is preferably 0.8 mm; and a diameter of a front end surface of the tapered portion 322a ranges from 0.35 mm to 0.6 mm. Preferably, an axial dimension of the tapered portion 322a accounts for 30% to 40% of an axial dimension of the rotational atherectomy head 322, an axial dimension of the cylindrical segment 321a accounts for 40% to 50% of the axial dimension of the rotational atherectomy head 322, and a ratio of a diameter of the cylindrical segment 321a to an axial dimension of the eccentric structure 321 ranges from 0.6 to 0.7.

Because a radial size of the tapered head 322a is smaller than radial sizes of the cylindrical segment 321a and the eccentric cone segment, the arrangement of the tapered portion 322a further makes it convenient to push a part of the plaque onto the outer wall surface of the rotational atherectomy head for rotational atherectomy.

Compared with other rotational atherectomy heads in the related art, the structure form of the rotational atherectomy head provided in this application can enable the size of the flexible shaft to be smaller in the radial direction, and the volume of the entire rotational atherectomy head is small. Therefore, even if the plaque is large, the rotational atherectomy head easily reaches the center of the plaque while still ensuring an excellent cutting effect. Further, during surgery, due to a small size of the entire rotational atherectomy head in a radial direction of the flexible shaft, the volume and the mass are relatively small. When the rotational atherectomy head rotates around the axis of the drive shaft assembly, self-rotation of the rotational atherectomy head drives surrounding blood to move. A fluid pressure field formed by the blood movement drives the rotational atherectomy head to rotate circumferentially around the inner wall of the blood vessel. In other words, while rotating around the axis of the rotational atherectomy head, the rotational atherectomy head revolves around the inner wall of the blood vessel. As an amount of plaque that is ground is increasingly large, a diameter of an inner cavity space of the blood vessel is also increasingly large, and a diameter of an orbit in which the rotational atherectomy head revolves is also gradually increased, thereby gradually grinding the plaque.

Through the structural form of the rotational atherectomy head of this application, as the rotational atherectomy head revolves, the rotational atherectomy head grinds the plaque in the circumferential direction of the blood vessel, instead of always grinding a position in the circumferential direction of the blood vessel. In this way, the increase in the blood temperature caused by the grinding can be reduced as much as possible. In addition, although the drive shaft rotates at a high speed, because the rotational atherectomy head rotates and revolves simultaneously, and the volume and mass of the rotational atherectomy head are relatively small, the rotational atherectomy head has a grinding force that is relatively small compared with a rotational atherectomy head with a major diameter, and can be reduced by a margin of more than 5%, thereby reducing impact on the blood vessel. In addition, in this application, the flexible shaft is arranged in a structure with two layers wound in opposite directions. In this way, when the flexible shaft is rotated in opposite directions, the spring wires on the inner and outer layers interact with each other, so that the flexible shaft can be well prevented from being loosened. In addition, the structure with two layers opposite to each other can improve flexibility of the flexible shaft and ensure torque transmission compared with a structure with three or more layers that are wound. In addition, a diameter of the entire flexible shaft is not excessively large, which is conducive to movement in the blood vessel. Further, laser welding is performed on the two ends of the flexible shaft, so that the spring wires on the two ends are integrated, which can avoid looseness of the inner and outer layers and the spring wires on the layers during high-speed rotation and reverse rotation of the flexible shaft as much as possible, and dispense with a protective sleeve at an end portion of the flexible shaft, thereby increasing reliability of the drive shaft and improving assembly efficiency of the entire coronary artery rotational atherectomy intervention system. In addition, the rotational atherectomy head can be arranged at the end portion of the flexible shaft. When the flexible shaft comes into contact with the plaque, due to a grinding action of the rotational atherectomy head, a contact force between the flexible shaft and the plaque can be reduced, and impact of the flexible shaft on the blood vessel can be reduced. Otherwise, if the rotational atherectomy head is separated from the end portion of the flexible shaft, when the end portion of the flexible shaft touches the plaque, impact on the blood vessel is relatively large.

Preferably, after the infusion pump control element controls the infusion pump to start, the infusion pump state detection and transmission module sends a first indication signal to the controller module, to enable the controller module to confirm that the infusion pump is in the started state.

Preferably, the drive and control system further includes an optical coupler, the optical coupler is located between the infusion pump state detection and transmission module and the controller module, and the optical coupler receives the first indication signal, processes the first indication signal, and transmits the first indication signal to the controller module.

Signal transmission is usually in the form of electromagnetic waves, and different electromagnetic waves are prone to mutual interference. In this application, an optical coupler is arranged between the infusion pump state transmission module and the controller module, and unidirectional signal transmission can be implemented through processing of the optical coupler, so that electrical isolation is completely implemented between the input end and the output end, and the output signal has no impact on the input end, that is, does not interfere with the first indication signal. Therefore, the controller module can accurately identify the first indication signal, thereby being strong in anti-interference capability, being stable in operation, being non-contact, being long in service life, and being high in transmission efficiency.

Preferably, after the limit switch is closed, the limit switch state detection and transmission module sends a second indication signal to the controller module, to enable the controller module to confirm that the limit switch is in the closed state.

Specifically, the limit switch and the limit switch state detection and transmission module may be integrated into the same displacement sensor. When the guide wire is clamped, (the limit switch state detection and transmission module in) the displacement sensor sends a second indication signal to the controller module.

Preferably, the drive and control system further includes a motor drive module and a speed detection module, the controller module is connected to both the motor drive module and the speed detection module, the drive motor is connected to both the motor drive module and the speed detection module, the motor drive module drives the drive motor under the control of the controller module, and the speed detection module feeds back real-time speed information of the drive motor to the controller module; and when a rotation speed of the drive motor measured in real time is greater than or less than a preset speed, the controller module in the drive and control system controls the motor drive module to adjust the rotation speed of the drive motor to the preset speed.

the coronary artery rotational atherectomy intervention system provided in this application can implement feedback control of the rotation speed of the drive motor, so that when being at an excessively high/low speed, the drive motor can return to the standard rotation speed. Specifically, in the speed detection module, there is a speed detection device, for example, a Hall sensor. The Hall sensor may measure a rotation speed of the motor in real time. When the rotation speed of the motor is greater than or less than a preset speed, the controller module adjusts a PWM pulse sent by the controller module. After receiving the foregoing pulse, the motor drive module adjusts the rotation speed of the drive motor to the preset speed (for example, the rotation speed of the motor may be adjusted by increasing or decreasing a current of the motor), thereby implementing feedback control of the rotation speed of the drive motor. The entire rotation speed adjustment process of the motor may be automatically implemented in a PID control manner.

Preferably, the drive and control system further includes a display screen 60, a multi-range knob switch 61, a range information processing module, and a motor drive module, where the multi-range knob switch is connected to the range information processing module, the range information processing module is connected to the controller module, the controller module is connected to the motor drive module, the motor drive module is connected to the drive motor 50 to control a rotation speed of the drive motor 50 to be in a selected range, and the display screen 60 is arranged at an angle of 30 degrees to a horizontal plane, and is configured to display the rotation speed of the drive motor and a rotational atherectomy time.

A plurality of ranges may be selected for a rotation speed of the drive motor of the coronary artery rotational atherectomy intervention system in this application, that is, the drive motor 50 may be set to rotate at different standard rotation speeds. Specifically, after the multi-range knob switch 61 is rotated to a selected range by an operator, specific code information corresponding to the selected range can be outputted for the selected range (that is, different code information is correspondingly outputted for different selected ranges). After receiving the code information, the range information processing module compares the code information with correspondences between code information stored in the range information processing module and ranges to determine a range that is selected, and then the controller module connected to the range information processing module may control the motor drive module to adjust the speed of the motor to a speed value corresponding to the range.

Preferably, the drive and control system further includes a sampling resistor, a sampling resistor voltage collection module, an amplifier, an amplified voltage information transmission module, and a motor drive module, where the drive motor is connected to the sampling resistor, the sampling resistor is connected to the sampling resistor voltage collection module, the sampling resistor voltage collection module is connected to the amplifier, the amplifier is connected to the amplified voltage information transmission module, the amplified voltage information transmission module is connected to the controller module, the controller module is connected to the motor drive module, the motor drive module is connected to the drive motor 50, and when overload occurs, the controller module controls the motor drive module to stop driving the drive motor 50, to cause the drive motor to stop running.

The coronary artery rotational atherectomy intervention system has an overload protection function that is implemented by using the foregoing technical solution. In a circuit of the drive and control system, a sampling resistor connected in series is arranged. A resistance value of the sampling resistor may be, for example, a small resistance value of 50 milliohms, to minimize impact on the original circuit. In this way, a voltage between two ends of the sampling resistor is not easy to be accurately measured. Therefore, in this application, the sampling resistor voltage collection module is connected to an amplifier, the amplifier amplifies the voltage value collected by the sampling resistor voltage collection module, and then transmits the amplified voltage value to the controller module. The controller module determines, based on the received voltage value, whether an overload condition occurs in the circuit. When the voltage value is greater than a predetermined voltage, it indicates that a current in the circuit is excessively high, that is, an overload condition occurs. When an overload condition occurs, the controller module controls the motor drive module to stop driving the drive motor 50, so that the drive motor 50 stops rotating, thereby implementing the overload protection function.

Preferably, the drive and control system further includes a motor drive module; the physiological saline infusion system further includes a plurality of flow rate adjustment circuits and a physiological saline infusion control motor (which are usually located outside the housing 10 and are not shown in the figure), the plurality of flow rate adjustment circuits include a plurality of resistors and a plurality of flow rate selector switches, resistance values of the plurality of resistors are different from each other, quantities of the flow rate adjustment circuits, the flow rate selector switches, and the resistors are the same, one flow rate selector switch and one resistor are serially connected in a same flow rate adjustment circuit, and each flow rate adjustment circuit is connected to the controller module; and the controller module is connected to the physiological saline infusion control motor, to control a rotation speed of the physiological saline infusion control motor, to further control an infusion speed of physiological saline.

There are at least two flow rates for the physiological saline. One flow rate is an ordinary flushing speed, which means that in a state in which the rotational atherectomy head of the coronary artery rotational atherectomy intervention system is inside a human body but is not rotating at a high speed to perform rotational atherectomy on a plaque, the flow rate of the physiological saline is the ordinary flushing speed, and flushing is performed at the ordinary flushing speed uninterruptedly, to prevent blood from flowing back into the interior of the coronary artery rotational atherectomy intervention system; and the other flow rate is a high-speed infusion speed, which means that in a state in which the rotational atherectomy head rotates at a high speed inside the human body to perform rotational atherectomy on the plaque, the flow rate of the physiological saline is the high-speed infusion speed higher than the ordinary flushing speed, to fully cool the rotational atherectomy head while preventing blood from flowing backwards. To enable the physiological saline to work at at least two different flow rates, a plurality of flow rate adjustment circuits (at least two) are arranged in the physiological saline control system. Each flow rate adjustment circuit includes a flow rate selector switch and a resistor. Through opening and closing of the flow rate selector switch, different flow rate adjustment circuits are in different path states. In this way, currents are different in different paths due to different resistance values of the resistors. The controller module can determine, according to different received current signals, flow rates that are selected by the operator and that correspond to the current signals, and control the infusion speed of the physiological saline by controlling the rotation speed of the physiological saline infusion control motor.

Preferably, the physiological saline infusion control motor drives the infusion pump, a rotation speed of the infusion pump is increased or decreased as the rotation speed of the physiological saline infusion control motor is increased or decreased, and the infusion speed of the physiological saline is increased or decreased as the rotation speed of the infusion pump is changed, to control the infusion speed of the physiological saline.

Preferably, stiffness of the guide wire 20 is less than stiffness of the flexible shaft 32, so that the guide wire 20 can better adapt to an extending path of the blood vessel.

To reduce damage to the blood vessel, in this application, although the rotation speed of the drive shaft may reach a high rotation speed ranging from 170,000 to 250,000 revolutions per minute, this high rotation speed is generally used only in a rotational-grinding state of the coronary artery rotational atherectomy intervention system, and in a non-rotational-grinding state, the rotation speed is set to be relatively low. Certainly, in the rotational-grinding state, a rotation speed ranging from 170,000 to 250,000 revolutions per minute is not always used, and a lower rotation speed such as 7000 revolutions per minute or 9000 revolutions per minute may also be set.

The spiral winding direction of the outer spring wire in the flexible shaft 32 may be the same as or opposite to a rotation direction of the drive shaft in the drive motor 50. In a preferred embodiment, the spiral winding direction of the outer spring wire is the same as a rotation direction of the drive shaft of the drive motor in a grinding state, so that during a grinding operation, the flexible shaft can be better in a tightly wound state, and a torque can be better transmitted, thereby increasing a grinding speed.

When the flexible shaft 32 rotates at a high speed, friction occurs between the flexible shaft 32 and the guide wire 20 passing through the flexible shaft. To reduce wear of the flexible shaft and the guide wire, an inner surface of the flexible shaft 32 and an outer surface of the guide wire 20 may be each provided with a wear-resistant coating, which may be specifically formed on the inner surface of the flexible shaft 32 and the outer surface of the guide wire 20 in a manner such as surface treatment or spraying. The wear-resistant coating may be a polytetrafluorethylene coating.

Preferably, the drive shaft assembly includes a drive shaft 30 and a drive shaft sleeve; the drive and control system further includes a driving gear and a transmission gear, a part of the drive shaft 30 is fixedly mounted in the transmission gear, and at least one part of remaining parts of the drive shaft that are not fixedly mounted in the transmission gear, and at least one part of the guide wire are located in the drive shaft sleeve; the drive shaft sleeve includes a front sleeve and a rear sleeve, the front sleeve includes a front moving rail tube 41 and a front static rail tube 42 that are nested, and the front sleeve is located in front of the transmission gear; and the rear sleeve includes a rear moving rail tube 43 and a rear static rail tube 44 that are nested, and the rear sleeve is located behind the transmission gear.

Preferably, there is a first wear-resistant tube (not shown in the figure) between the drive shaft 30 and the front moving rail tube 41.

Preferably, there is a second wear-resistant tube (not shown in the figure) between the drive shaft 30 and the rear moving rail tube 43.

Preferably, a wear-resistant coating is provided on at least one part of an outer surface of the drive shaft 30.

Preferably, a flexible seal ring 45 is arranged outside the front moving rail tube, where an inner diameter of the seal ring is less than an outer diameter of the front moving rail tube in a natural state; and a flexible seal ring 45 is arranged outside the rear moving rail tube, where an inner diameter of the seal ring is less than an outer diameter of the rear moving rail tube in a natural state.

Specifically, the rigid shaft 31 in the drive shaft 30 is inserted and connected to the transmission gear, so that a part of the drive shaft is fixedly mounted to the transmission gear and is in interference fit with the transmission gear, to transmit the driving power of the drive motor to the rigid shaft 31. An axial direction of the rigid shaft is parallel to a sliding direction of a driving mechanism, and is specifically parallel to an axial direction of the drive shaft of the drive motor and a rotational axis of the transmission gear.

Figure 2:
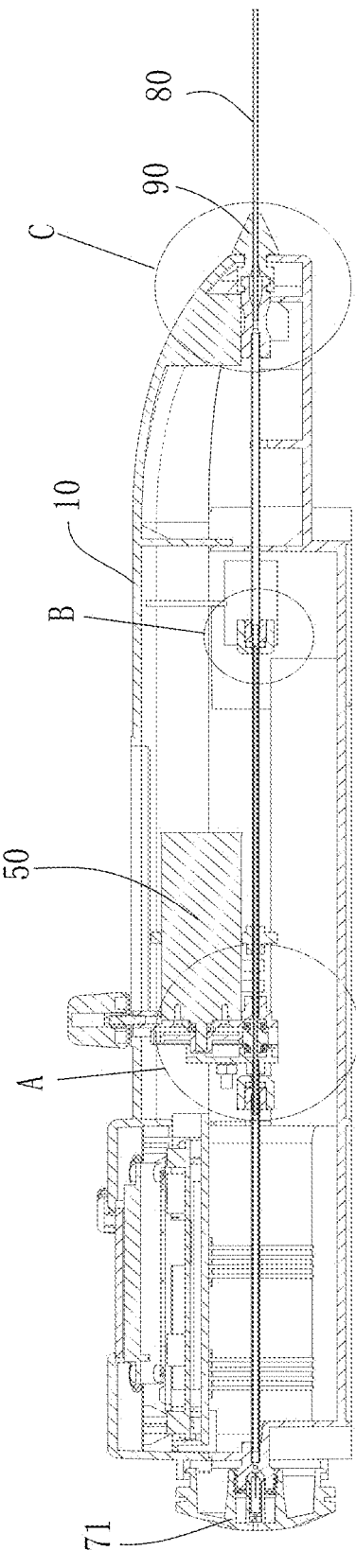
FIG. 2 is a cross-segmental schematic structural diagram of the coronary artery rotational atherectomy intervention system in FIG. 1 with a flexible shaft and a guide wire being removed.
Figure 3:
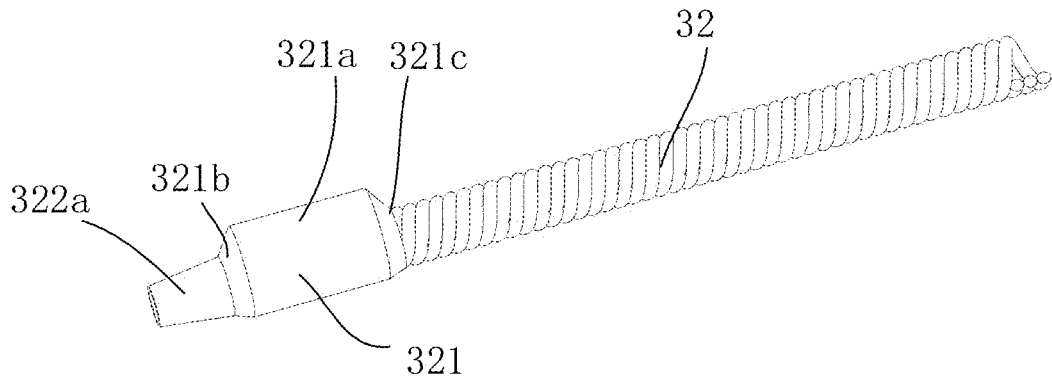
FIG. 3 is a three-dimensional schematic structural diagram of a preferred implementation of a part of a flexible shaft and a rotational atherectomy head according to this application.
Figure 4:
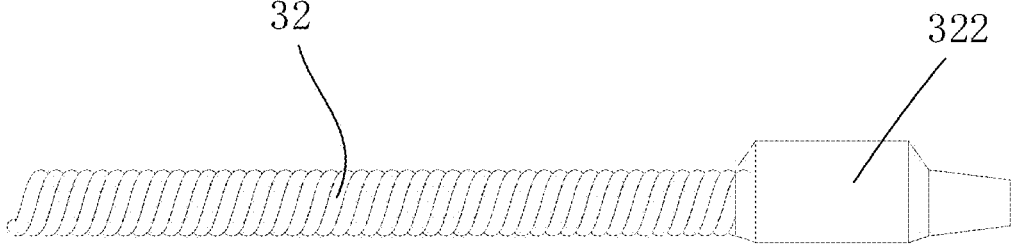
FIG. 4 is a right view of a preferred implementation of a part of a flexible shaft and a rotational atherectomy head of this application.
Figure 5:
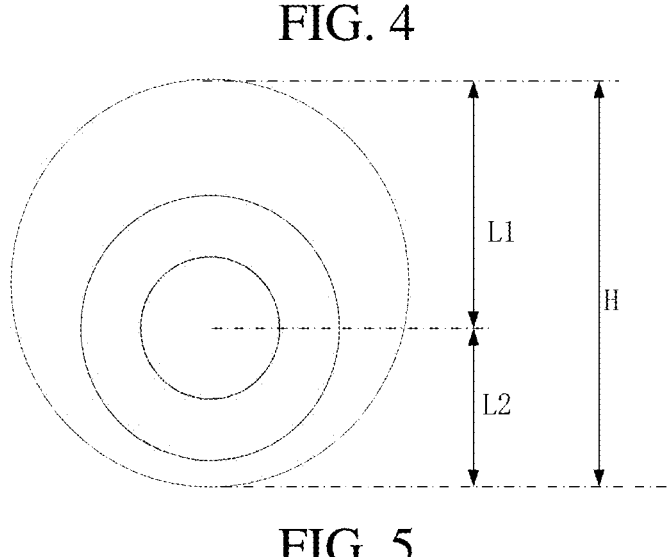
FIG. 5 is a front view of a preferred implementation of a part of a flexible shaft and a rotational atherectomy head of this application.
Figure 6:
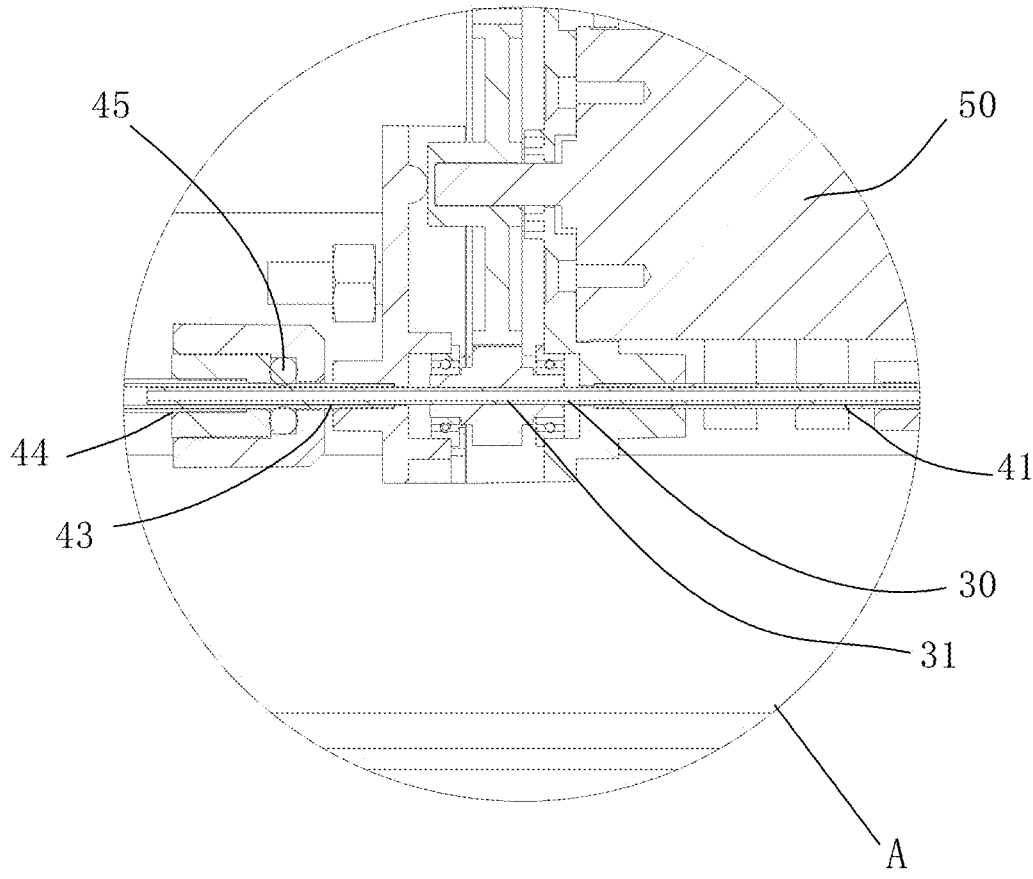
FIG. 6 is a partially enlarged schematic structural diagram of a position A in FIG. 1.

A person skilled in the art may understand that, the drive shaft 30 is a hollow shaft and the guide wire 20 penetrates through the drive shaft 30. As the driving mechanism slides forward, the drive shaft 30 slides forward relative to the housing 10, but may bend or have another fault during movement, and cannot slide in a predetermined direction, increasing difficulty of control. In a process of pulling back the drive shaft, the drive shaft and the guide wire may also bend, thereby preventing the drive shaft from retracting. In this application, the drive shaft sleeve is arranged, to constrain and guide the drive shaft and the guide wire. Referring to FIG. 2, FIG. 6, and FIG. 7, a part of the rigid shaft 31 in the drive shaft 30 is inserted into the transmission gear below the drive motor by interference, a part of the drive shaft located in front of the transmission gear is arranged in the front sleeve, and a part of the drive shaft located behind the transmission gear and the guide wire are arranged in the rear sleeve. Both the front sleeve and the rear sleeve are arranged in an axial direction of a drive shaft located at the transmission gear, the front sleeve is located in front of the transmission gear, and the rear sleeve is located behind the transmission gear. Sleeve support bases are arranged at intervals on the bottom wall of the housing to support the front sleeve and the rear sleeve in extending in the axial direction.

The front sleeve includes a front moving rail tube 41 and a front static rail tube 42 that are nested to form a set of sliding pairs. In this embodiment, the front moving rail tube 41 is arranged inside the front static rail tube 42. A part of the drive shaft located in front of the transmission gear is inlaid in an inner cavity of the front moving rail tube 41 in a manner of being fixed relative to the front moving rail tube. There is a first wear-resistant tube between the drive shaft and the front moving rail tube 41 to reduce a friction force between the drive shaft and the front moving rail tube.

The rear sleeve includes a rear moving rail tube 43 and a rear static rail tube 44 that are nested to form a set of sliding pairs. In this embodiment, the rear moving rail tube 43 is arranged inside the rear static rail tube 44. A part of the drive shaft located behind the transmission gear is inlaid in an inner cavity of the rear moving rail tube 43 in a manner of being fixed relative to the rear moving rail tube. There is a second wear-resistant tube between the drive shaft and the rear moving rail tube 43 to reduce a friction force between the drive shaft and the rear moving rail tube.

A wear-resistant coating may be further provided on at least one part of the outer surface of the drive shaft, to reduce a friction force between the drive shaft and a component adjacent to the drive shaft during movement of the drive shaft.

A sliding groove is provided inside the coronary artery rotational atherectomy intervention system in this application. The front moving rail tube 41 and the rear moving rail tube 43 can slide along the sliding groove, to ensure that the drive shaft smoothly advances and retracts in the axial direction, so that the rotational atherectomy head is transferred to the plaque to be rotationally ground, and the rotational atherectomy head is retracted after the rotational atherectomy ends, thereby effectively ensuring the safety and reliability of the rotational atherectomy and excision surgery of the plaque.

A person skilled in the art may understand that, when tube walls have the same thickness, because the outer diameters of the moving rail tubes on the two sides and the outer diameters of the static rail tubes on the two sides are greater than the outer diameter of the drive shaft, the bending strengths of the moving rail tubes on the two sides and the bending strengths of the static rail tubes on the two sides are greater than the bending strength of the drive shaft. In addition, the moving rail tubes on the two sides and the static rail tubes on the two sides are not configured to extend into a blood vessel of a human body, and according to the invention objective of this application, as opposed to requiring ease of bending, the moving rail tubes on the two sides and the static rail tubes on the two sides require sufficiently high bending strengths. Therefore, when the tube walls are thinner than or equal to the tube wall of the drive shaft, the moving rail tubes on the two sides and the static rail tubes on the two sides may be made of a material with a higher strength, such as 304 stainless steel.

The first wear-resistant tube/second wear-resistant tube is optionally made of a medical polyimide material, which has advantages of a low surface friction coefficient and high temperature resistance. While the friction force during relative sliding is reduced, a gap between the drive shaft and the front moving rail tube/rear moving rail tube can be further filled through arrangement of the first wear-resistant tube/second wear-resistant tube, thereby reducing a rate at which the physiological saline leaks backward from the physiological saline infusion system located in front of the front moving rail tube.

Through the arrangement of the drive shaft sleeve, the axial guidance effect is enhanced, the front moving rail tube or the front static rail tube may further constrain the drive shaft on the radially inner side, to prevent the drive shaft from being excessively bent, and the rear static rail tube may constrain both the guide wire and the drive shaft in the radial direction, thereby ensuring smooth transmission of the axial thrust to the rotational atherectomy head arranged at the distal end of the drive shaft, that is, ensuring smooth forward advancement and retraction of the drive shaft in the axial direction, and further ensuring the safety of the rotational atherectomy and excision surgery.

As described above, the coronary artery rotational atherectomy intervention system has a physiological saline infusion system. The physiological saline infused through the system finally enters a drive shaft sleeve assembly, and flows along a cavity inside the drive shaft sleeve assembly, to reduce a temperature of the drive shaft 30 located inside the drive shaft sleeve, and in particular, a temperature of the rotational atherectomy head 322 on a part of the flexible shaft 32 of the drive shaft 30. A flexible seal ring 45 is arranged outside the front moving rail tube, where an inner diameter of the seal ring 45 is less than an outer diameter of the front moving rail tube in a natural state 41; and a flexible seal ring 45 is arranged outside the rear moving rail tube 43, where an inner diameter of the seal ring 45 is less than an outer diameter of the rear moving rail tube 43 in a natural state. Therefore, the possibility of leakage of the physiological saline can be effectively reduced, so that the physiological saline only flows out through the interior of the drive shaft sleeve assembly to an end of the following intervention catheter as much as possible, thereby preventing the physiological saline from leaking into the housing of the coronary artery rotational atherectomy intervention system to affect the normal operation of the coronary artery rotational atherectomy intervention system.

Figure 9:
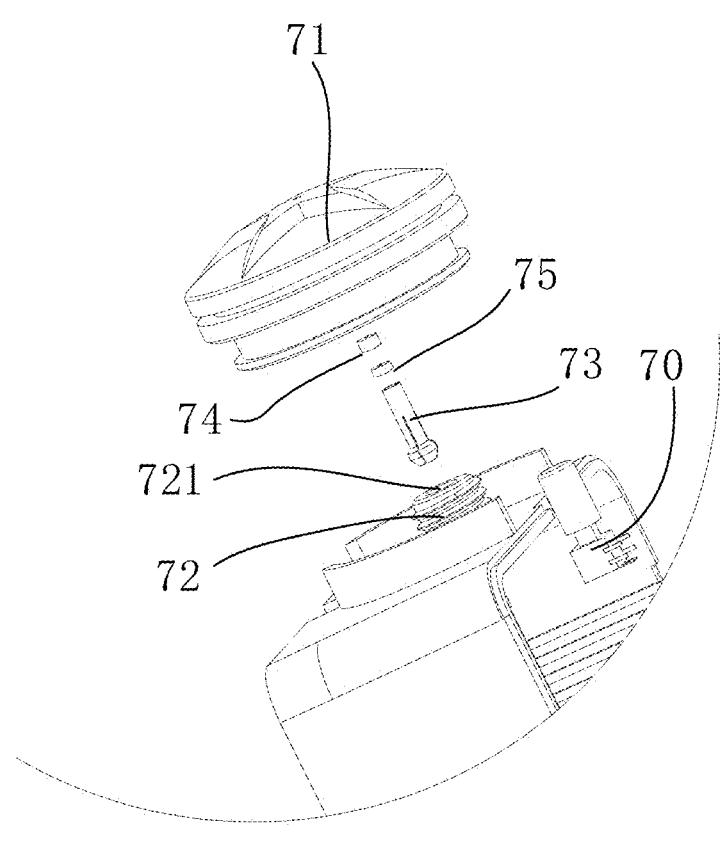
FIG. 9 is an exploded schematic structural diagram of a coronary artery rotational atherectomy intervention system at a guide wire clamping system according to this application.
Figure 10:
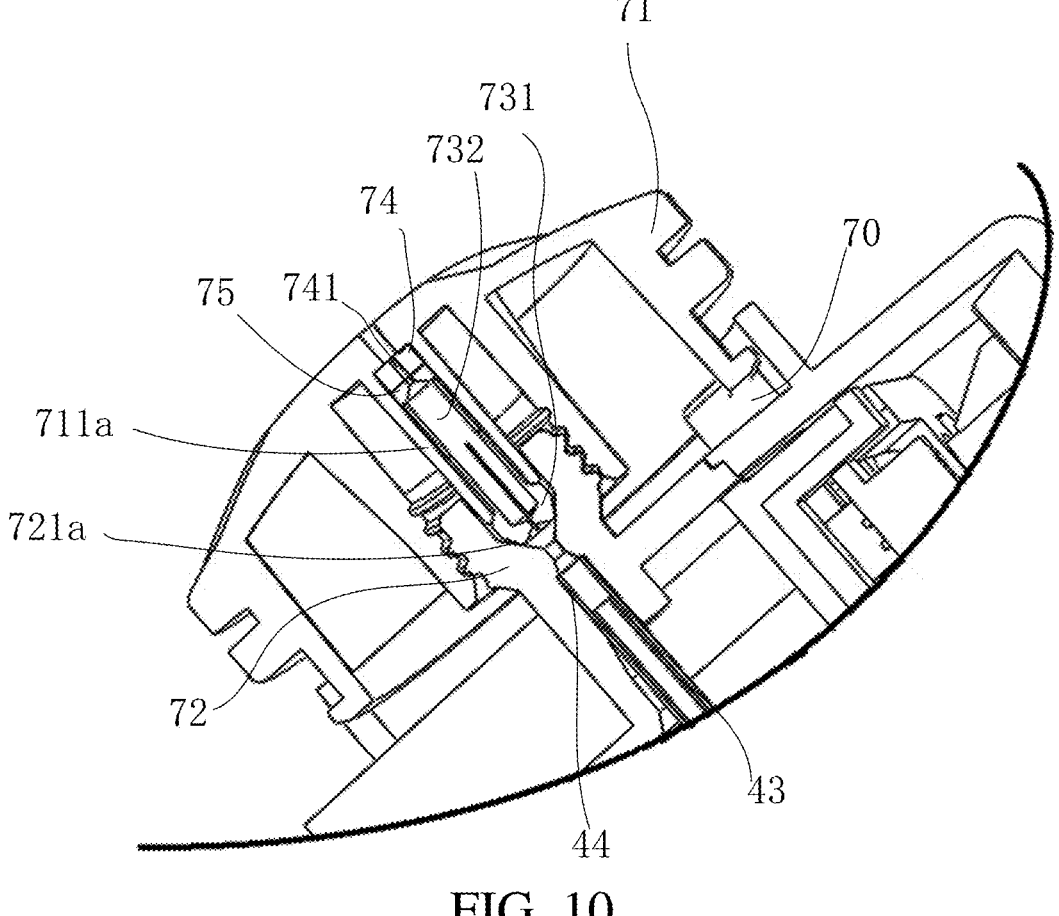
FIG. 10 is a cross-segmental schematic structural diagram of a coronary artery rotational atherectomy intervention system at a guide wire clamping system according to this application.

Preferably, referring to FIG. 9 and FIG. 10, the limit switch 70 is fixed relative to a rear wall of a housing 10 of the coronary artery rotational atherectomy intervention system, and extends out of the rear wall; and the guide wire clamping system includes a multi-claw chuck 73, a chuck cover 71, and a chuck cover fixing base 72, where the multi-claw chuck 73 includes a chucking portion 731 formed by a plurality of independent claws and a body portion 732 that is configured to fixedly connect the plurality of independent claws, the body portion 732 is arranged inside the chuck cover 71, and the chucking portion 731 extends into the chuck cover fixing base 72; the chuck cover fixing base 72 is fixed relative to the rear wall, a part of the chuck cover fixing base 72 located behind the rear wall has an external thread, a rear opening 721 of the chuck cover fixing base 72 is configured for the chucking portion 731 to extend, and the rear opening 721 includes a tapered multi-claw chuck clamping portion 721*a*; an internal thread matching the external thread exists inside the chuck cover 71, and the chuck cover 71 is fixed on the chuck cover fixing base 72 through the matching between the internal thread and the external thread; the multi-claw chuck 73 is elastic, the chucking portion 731 of the multi-claw chuck 73 can be opened after the guide wire 20 is inserted into the multi-claw chuck 73, interference fit can be formed between the multi-claw chuck clamping portion 721*a* and the opened chucking portion 731 after the chuck cover 71 is tightened relative to the chuck cover fixing base 72, and the interference fit clamps the chucking portion 731, to cause the guide wire 20 to be clamped by the multi-claw chuck 73; and after the chuck cover 71 is tightened relative to the chuck cover fixing base 72, a front end surface of the chuck cover 71 presses the limit switch 70, to trigger the limit switch 70 to be in the closed state.

Specifically, the multi-claw chuck is, for example, a four-claw chuck or a three-claw chuck, and may be similar in shape to a cross round head bolt. An opening is provided in the four-claw chuck from a rear end surface forward. The opening extends into a bolt head. The bolt head is provided with a "cross"-shaped slot. In a radial direction, the "cross"-shaped slot extends all the way to a radial outer edge of the bolt head. The "cross"-shaped slot further extends in a length direction, and extends all the way to a body portion of the bolt (the body portion of the bolt does not include the bolt head), but does not run through the body portion of the bolt, thereby forming a four-claw chuck in which a front end includes four clamping claws and the four clamping claws are sequentially arranged in a circumferential direction. In this case, four independent claws form the chucking portion, and a part located behind the four independent claws is a body portion of the multi-claw chuck.

After the chuck cover 71 is tightened relative to the chuck cover fixing base 72, two results are generated. First, due to the foregoing tightening, the multi-claw chuck 73 is advanced forward and squeezed into the multi-claw chuck clamping portion 721*a* whose inner surface is tapered. In this way, interference fit is formed between the multi-claw chuck clamping portion 721*a* and the opened chucking portion 731. The interference fit clamps the chucking portion 731, so that the guide wire 20 clamped in the chucking portion 731 is clamped by the multi-claw chuck 73. Second, due to the foregoing tightening, the front end face of the chuck cover 71 changes from being unable to come into contact with the rear end face of the limit switch 70 to being able to come into contact with and press the rear end face of the limit switch 70, thereby triggering the limit switch 70 to be in the closed state (for example, two compression springs that are not in contact with each other may be arranged in the limit switch in an implementation, where because the two compression springs are in contact with each other due to being pressed after the limit switch is pressed by the front end face of the chuck cover, that is, the limit switch is closed, the two compression springs are in contact with each other to form a circuit path, and the closed state of the limit switch can be detected by the limit switch detection and transmission module).

Preferably, the chuck cover 71 includes a cylindrical first stop structure 711, a second stop structure 75 is further arranged inside the chuck cover 71, and after the chuck cover 71 is tightened relative to the chuck cover fixing base 72, the first stop structure 711 and the second stop structure 75 are configured to stop the multi-claw chuck 73 from moving backward.

The first stop structure 711 may be a cylindrical structure inside the chuck cover. The cylindrical structure may be integrally formed with the chuck cover. An inner diameter of the cylinder is slightly greater than an outer diameter of the body portion of the similar cross round head bolt, but less than a diameter of a bottom portion of the bolt head of the bolt. Therefore, after the chuck cover is tightened relative to the chuck cover fixing base, the body portion of the bolt is located in the cylinder, and a front end surface of the cylinder abuts against the bottom portion of the bolt head due to the foregoing tightening, to block the multi-claw chuck from moving backward.

The second stop structure 75 may be located behind the multi-claw chuck 73, a front end surface of the second stop structure 75 abuts against a rear end surface of the multi-claw chuck 73, and a rear end surface of the second stop structure 75 is directly or indirectly limited by the chuck cover 71. Therefore, the second stop structure 75 can also stop the multi-claw chuck 73 from moving backward. A through hole is provided in the second stop structure 75. The through hole may include a horn hole portion and a constant diameter hole portion. The horn hole portion is closer to the rear end surface of the multi-claw chuck 73 than the constant diameter hole portion is. A diameter of the constant diameter hole portion is equal to a diameter of a rear end of the horn hole portion. In this way, the guide wire can be guided to smoothly pass through the through hole in the second stop structure.

Preferably, the guide wire clamping system further includes a flexible sealing structure 74, the flexible sealing structure 74 includes a first via 741 for the guide wire to pass through, a diameter of the first via 741 is not greater than a diameter of the guide wire 20 in a natural state, the flexible sealing structure 74 is located inside the chuck cover 71 and behind the second stop structure 75, and a front end surface of the flexible sealing structure 74 abuts against a rear end surface of the second stop structure 75.

The flexible sealing structure 74 may be made of a silicone material. It can be understood that, the diameter of the first via 741 is not greater than an outer diameter of the guide wire 20, but allows the guide wire 20 to pass through the first via. After the chuck cover 71 is tightened relative to the chuck cover fixing base 72, the flexible sealing structure 74 is compressed and deformed, to further compress the guide wire 20, and a gap between the guide wire 20 and the flexible sealing structure 74 is further reduced, thereby achieving a sealing effect, and preventing physiological saline (if any) leaking from the drive shaft sleeve into the housing of the coronary artery rotational atherectomy intervention system from flowing out of the coronary artery rotational atherectomy intervention system through the first via 741 between the guide wire 20 and the flexible sealing structure 74.

Through the specific arrangement of the foregoing guide wire clamping system, the guide wire can be effectively clamped, thereby preventing the guide wire from being displaced during the working of the coronary artery rotational atherectomy intervention system to cause a medical accident.

Preferably, the drive and control system further includes a timing module and an alarm apparatus that are connected to the controller module, the timing module is configured to time rotation of the drive motor, and when a single rotation time of the drive motor reaches first preset duration or a plurality of accumulated rotation times reaches second preset duration, the controller module controls the alarm apparatus to issue an alarm.

The coronary artery rotational atherectomy intervention system further includes an intervention catheter mechanism. The intervention catheter mechanism has one part located inside the housing and the other part extending out from a front end of the housing. In addition to the rear wall mentioned above, the housing further includes a front wall and a bottom wall. A second via 11 is provided on the front wall.

The intervention catheter mechanism includes an intervention catheter 80 and an adapter 90, a part of the drive shaft is located inside the intervention catheter, an adapter through hole is provided in the adapter 90, and a rear end of the intervention catheter 80 is inserted into the adapter through hole to be in interference fit with the adapter through hole.

The adapter 90 includes an adapter front 91, an adapter diameter reduction structure 92, and an adapter rear 93. The adapter front 91 is exposed to the outside of the housing 10. The adapter front 91 is a cone made of a flexible material, which has an aesthetic structure and facilitates protection of the intervention catheter 80, so that the intervention catheter 80 is not prone to bending under force. The adapter diameter reduction structure 92 is located between the adapter front 91 and the adapter rear 93, and a minimum diameter of the adapter diameter reduction structure 92 is smaller than a minimum diameter of the adapter front 91 and a minimum diameter of the adapter rear 93. The size of the second via 11 on the front end surface of the housing 10 matches the size of the adapter diameter reduction structure 92, so that the adapter diameter reduction structure 92 can be stuck at the second via 11, thereby fixing the adapter 90 on the housing 10.

The physiological saline infusion system further includes an output connector 100 and a water inlet pipeline (the water inlet pipeline is not shown in the figure). An end of the water inlet pipeline is inserted into a side wall of the output connector 100 to form interference fit, to reliably fix the water inlet pipeline and avoid leakage of the physiological saline at the water inlet pipeline as much as possible.

Further, the rear end of the intervention catheter 80 may further completely pass through the through hole in the adapter 90, to extend into the output connector 100 of the physiological saline infusion system. Therefore, after entering the output connector 100 from the inlet water pipeline, the low-temperature physiological saline can quickly enter the intervention catheter 80, and then enter the blood vessel of the human body along the intervention catheter 80, thereby cooling the rotational atherectomy head 322 in the working state. Further, a first snap fit structure is arranged inside the adapter rear and outside a front end of the output connector, so that the adapter 90 and the output connector 100 can be fixed together.

The first snap fit structure includes a snap head 102 and a snap groove, the snap groove is provided inside the adapter rear 93, and the snap head 102 is arranged at a front end of the output connector 100 and matches the snap groove. To facilitate mounting of the snap head 102 into the snap groove, a junction of a front end surface and the side wall of the output connector 100 is provided with a chamfer, and an angle of the chamfer may range from 30° to 60°.

The output connector 100 includes an output connector body portion 101 and the snap head 102, and the snap head 102 is located in front of the output connector body portion 101. The output connector body portion 101 includes an output connector front 103, an output connector diameter reduction portion 104, and an output connector rear 105. A first slope transition segment is provided between the output connector diameter reduction portion 104 and the output connector front 103, and a second slope transition segment is provided between the output connector diameter reduction portion 104 and the output connector rear 105. There is a through hole inside the output connector. The through hole may be variable in diameter. A part of the through hole in contact with the foregoing intervention catheter can achieve interference fit to clamp an end of the intervention catheter, and a part of the through hole in contact with the following front static rail tube can also achieve interference fit to clamp a front end of the front static rail tube.

An output connector support base is arranged on an upper surface of the bottom wall of the housing of the coronary artery rotational atherectomy intervention system, and the output connector support base is configured to support the output connector front.

In the coronary artery rotational atherectomy intervention system in this application, in addition to displaying the real-time rotation speed of the drive motor, the current rotation time, the accumulated rotation time, and the like, the display screen of the drive and control system may further display the temperature of the rotational atherectomy head. The display screen, the foregoing multi-range selection knob, and the like are all arranged at a rear end of the apparatus (located behind the physiological saline infusion system, and also behind the drive motor). This is based on ergonomic consideration. During surgery, an attending doctor is mainly responsible for operating instruments and observing CT imaging results, and jobs such as observing the display screen and operating the knob are completed by an assistant. The display screen and the knob are located at the rear end, which is convenient for the assistant to stand at an end of the machine in cooperation with the attending doctor in operation.

A person skilled in the art can understand that the foregoing preferred solutions can be freely combined and superimposed based on the premise that there is no conflict.

It should be understood that the foregoing implementations are merely exemplary but not limitative, and various obvious or equivalent modifications or replacements that may be made by a person skilled in the art to the foregoing details without departing from the basic principles of this application shall fall within the scope of the claims of this application.

What is claimed is:

1. A coronary artery rotational atherectomy intervention system, comprising a rotational atherectomy mechanism, a physiological saline infusion system, a drive and control system, and a guide wire clamping system, wherein the rotational atherectomy mechanism comprises a guide wire, a drive shaft assembly, and a rotational atherectomy head, wherein the guide wire clamping system comprises a limit switch and a limit switch state detection and transmission module, the limit switch is connected to the limit switch state detection and transmission module, and after the guide wire is clamped, the limit switch is triggered to be in a closed state and is detected by the limit switch state detection and transmission module;

the physiological saline infusion system comprises an infusion pump, an infusion pump control element, and an infusion pump state detection and transmission module, the infusion pump control element is connected to the infusion pump, the infusion pump control element is configured to control the infusion pump to be in a started state, and the infusion pump is connected to the infusion pump state detection and transmission module, to enable the started state of the infusion pump to be detected by the infusion pump state detection and transmission module;

the drive and control system comprises a drive motor and a controller module, and the limit switch state detection and transmission module and the infusion pump state detection and transmission module are separately connected to the controller module to transmit state data to the controller module; and the controller module confirms, before issuing an instruction for starting the drive motor, that the infusion pump of the physiological saline infusion system is in the started state and the limit switch is in the closed state, to cause the drive motor to rotate and then drive the rotational atherectomy head to rotate together through the drive shaft assembly.

2. The coronary artery rotational atherectomy intervention system according to claim 1, wherein the drive shaft assembly comprises a drive shaft, the drive shaft comprises a rigid shaft and a flexible shaft, the flexible shaft is fixedly connected to a front side of the rigid shaft, the rotational atherectomy head is formed at an end of the flexible shaft away from the rigid shaft, and the rotational atherectomy head comprises an eccentric structure in a circumferential direction around the flexible shaft; the eccentric structure comprises a cylindrical segment, and in different radial directions of a cross segment of the cylindrical segment, a connecting line between a first point on an outer wall surface of the cylindrical segment closest to a central axis of the flexible shaft and a second point on the outer wall surface of the cylindrical segment farthest from the central axis of the flexible shaft intersects with the central axis of the flexible shaft; and a straight-line distance between the first point and the second point ranges from 0.8 mm to 1.2 mm, and a difference between a distance from the second point to the central axis and a distance from the first point to the central axis ranges from 0.05 mm to 0.2 mm.

3. The coronary artery rotational atherectomy intervention system according to claim 2, wherein the straight-line distance between the first point and the second point is 0.9 mm, and the difference between the distance from the second point to the central axis and the distance from the first point to the central axis is 0.1 mm.

4. The coronary artery rotational atherectomy intervention system according to claim 3, wherein the rotational atherectomy head further comprises a tapered portion located at a front end of the eccentric structure, the tapered portion is coaxial with the flexible shaft, a major diameter end of the tapered portion is connected to the eccentric structure, and the eccentric structure further comprises a first eccentric cone segment and a second eccentric cone segment located at a front end and a rear end of the cylindrical segment respectively, wherein a minor diameter end of the first eccentric cone segment is connected to the major diameter end of the tapered portion, a major diameter end of the first eccentric cone segment is connected to the front end of the cylindrical segment, a major diameter end of the second eccentric cone segment is connected to the rear end of the cylindrical segment, and a minor diameter end of the second eccentric cone segment is connected to an outer circumferential surface of the flexible shaft; the tapered portion is made of stainless steel, and has an outer surface being a smooth surface; and the eccentric structure comprises an electroformed nickel substrate and abrasive particles inlaid in the substrate by electroplating.

5. The coronary artery rotational atherectomy intervention system according to claim 4, wherein an axial dimension of the tapered portion accounts for 30% to 40% of an axial dimension of the rotational atherectomy head, an axial dimension of the cylindrical segment accounts for 40% to 50% of the axial dimension of the rotational atherectomy head, and a ratio of a diameter of the cylindrical segment to an axial dimension of the eccentric structure ranges from 0.6 to 0.7.

6. The coronary artery rotational atherectomy intervention system according to claim 1, wherein after the infusion pump control element controls the infusion pump to start, the infusion pump state detection and transmission module sends a first indication signal to the controller module, to enable the controller module to confirm that the infusion pump is in the started state.

7. The coronary artery rotational atherectomy intervention system according to claim 6, wherein the drive and control system further comprises an optical coupler, the optical coupler is located between the infusion pump state detection and transmission module and the controller module, and the optical coupler receives the first indication signal, processes the first indication signal, and transmits the first indication signal to the controller module.

8. The coronary artery rotational atherectomy intervention system according to claim 1, wherein after the limit switch is closed, the limit switch state detection and transmission module sends a second indication signal to the controller module, to enable the controller module to confirm that the limit switch is in the closed state.

9. The coronary artery rotational atherectomy intervention system according to claim 1, wherein the drive and control system further comprises a motor drive module and a speed detection module, the controller module is connected to both the motor drive module and the speed detection module, the drive motor is connected to both the motor drive module and the speed detection module, the motor drive module drives the drive motor under the control of the controller module, and the speed detection module feeds back real-time speed information of the drive motor to the controller module; and when a rotation speed of the drive motor measured in real time is greater than or less than a preset speed, the controller module in the drive and control system controls the motor drive module to adjust the rotation speed of the drive motor to the preset speed.

10. The coronary artery rotational atherectomy intervention system according to claim 1, wherein the drive and control system further comprises a display screen, a multi-range knob switch, a range information processing module, and a motor drive module, wherein the multi-range knob switch is connected to the range information processing module, the range information processing module is connected to the controller module, the controller module is connected to the motor drive module, the motor drive module is connected to the drive motor to control a rotation speed of the drive motor to be in a selected range, and the display screen is arranged at an angle of 30 degrees to a horizontal plane, and is configured to display the rotation speed of the drive motor and a rotational atherectomy time.

11. The coronary artery rotational atherectomy intervention system according to claim 1, wherein the drive and control system further comprises a sampling resistor, a sampling resistor voltage collection module, an amplifier, an amplified voltage information transmission module, and a motor drive module, wherein the drive motor is connected to the sampling resistor, the sampling resistor is connected to the sampling resistor voltage collection module, the sampling resistor voltage collection module is connected to the amplifier, the amplifier is connected to the amplified voltage information transmission module, the amplified voltage information transmission module is connected to the controller module, the controller module is connected to the motor drive module, the motor drive module is connected to the drive motor, and when overload occurs, the controller module controls the motor drive module to stop driving the drive motor, to cause the drive motor to stop running.

12. The coronary artery rotational atherectomy intervention system according to claim 1, wherein the drive and control system further comprises a motor drive module; the physiological saline infusion system further comprises a plurality of flow rate adjustment circuits and a physiological saline infusion control motor, the plurality of flow rate adjustment circuits comprise a plurality of resistors and a plurality of flow rate selector switches, resistance values of the plurality of resistors are different from each other, quantities of the flow rate adjustment circuits, the flow rate selector switches, and the resistors are the same, one flow rate selector switch and one resistor are serially connected in a same flow rate adjustment circuit, and each flow rate adjustment circuit is connected to the controller module; and the controller module is connected to the physiological saline infusion control motor, to control a rotation speed of the physiological saline infusion control motor, to further control an infusion speed of physiological saline.

13. The coronary artery rotational atherectomy intervention system according to claim 12, wherein the physiological saline infusion control motor drives the infusion pump, a rotation speed of the infusion pump is increased or decreased as the rotation speed of the physiological saline infusion control motor is increased or decreased, and the infusion speed of the physiological saline is increased or decreased as the rotation speed of the infusion pump is changed, to control the infusion speed of the physiological saline.

14. The coronary artery rotational atherectomy intervention system according to claim 1, wherein the drive shaft assembly comprises a drive shaft and a drive shaft sleeve; the drive and control system further comprises a driving gear and a transmission gear, a part of the drive shaft is fixedly mounted in the transmission gear, and at least one part of remaining parts of the drive shaft that are not fixedly mounted in the transmission gear, and at least one part of the guide wire are located in the drive shaft sleeve; the drive shaft sleeve comprises a front sleeve and a rear sleeve, the front sleeve comprises a front moving rail tube and a front static rail tube that are nested, and the front sleeve is located in front of the transmission gear; the rear sleeve comprises a rear moving rail tube and a rear static rail tube that are nested, and the rear sleeve is located behind the transmission gear; and a first wear-resistant tube exists between the drive shaft and the front moving rail tube, and/or a second wear-resistant tube exists between the drive shaft and the rear moving rail tube, and/or a wear-resistant coating is provided on at least one part of an outer surface of the drive shaft.

15. The coronary artery rotational atherectomy intervention system according to claim 14, wherein a flexible seal ring is arranged outside the front moving rail tube, wherein an inner diameter of the seal ring is less than an outer diameter of the front moving rail tube in a natural state; and a flexible seal ring is arranged outside the rear moving rail tube, wherein an inner diameter of the seal ring is less than an outer diameter of the rear moving rail tube in a natural state.

16. The coronary artery rotational atherectomy intervention system according to claim 1, wherein the limit switch is fixed relative to a rear wall of a housing of the coronary artery rotational atherectomy intervention system, and extends out of the rear wall; and the guide wire clamping system comprises a multi-claw chuck, a chuck cover, and a chuck cover fixing base, wherein the multi-claw chuck comprises a chucking portion formed by a plurality of independent claws and a body portion that is configured to fixedly connect the plurality of independent claws, the body portion is arranged inside the chuck cover, and the chucking portion extends into the chuck cover fixing base;

the chuck cover fixing base is fixed relative to the rear wall, a part of the chuck cover fixing base located behind the rear wall has an external thread, a rear opening of the chuck cover fixing base is configured for the chucking portion to extend, and the rear opening comprises a tapered multi-claw chuck clamping portion;

an internal thread matching the external thread exists inside the chuck cover, and the chuck cover is fixed on the chuck cover fixing base through the matching between the internal thread and the external thread;

the multi-claw chuck is elastic, the chucking portion of the multi-claw chuck is opened after the guide wire is inserted into the multi-claw chuck, interference fit is formed between the multi-claw chuck clamping portion and the opened chucking portion after the chuck cover is tightened relative to the chuck cover fixing base, and the interference fit clamps the chucking portion, to cause the guide wire to be clamped by the multi-claw chuck; and after the chuck cover is tightened relative to the chuck cover fixing base, a front end surface of the chuck cover presses the limit switch, to trigger the limit switch to be in the closed state.

17. The coronary artery rotational atherectomy intervention system according to claim 16, wherein the chuck cover comprises a cylindrical first stop structure, a second stop structure is further arranged inside the chuck cover, and after the chuck cover is tightened relative to the chuck cover fixing base, the first stop structure and the second stop structure are configured to stop the multi-claw chuck from moving backward.

18. The coronary artery rotational atherectomy intervention system according to claim 17, wherein the guide wire clamping system further comprises a flexible sealing structure, the flexible sealing structure comprises a first via for the guide wire to pass through, a diameter of the first via is not greater than a diameter of the guide wire in a natural state, the flexible sealing structure is located inside the chuck cover and behind the second stop structure, and a front end surface of the flexible sealing structure abuts against a rear end surface of the second stop structure.

19. The coronary artery rotational atherectomy intervention system according to claim 1, wherein the drive and control system further comprises a timing module and an alarm apparatus that are connected to the controller module, the timing module is configured to time rotation of the drive motor, and when a single rotation time of the drive motor reaches first preset duration or a plurality of accumulated rotation times reaches second preset duration, the controller module controls the alarm apparatus to issue an alarm.

* * * * *